(12) United States Patent
Linker et al.

(10) Patent No.: US 8,429,987 B1
(45) Date of Patent: Apr. 30, 2013

(54) SCREENING PORTAL, SYSTEM AND METHOD OF USING SAME

(75) Inventors: Kevin L. Linker, Albuquerque, NM (US); John A. Hunter, Albuquerque, NM (US); Charles A. Brusseau, Tijeras, NM (US)

(73) Assignee: Sandia Corporation, Albuquerque, NM (US)

( * ) Notice: Subject to any disclaimer, the term of this patent is extended or adjusted under 35 U.S.C. 154(b) by 401 days.

(21) Appl. No.: 12/636,852

(22) Filed: Dec. 14, 2009

(51) Int. Cl.
*G01N 1/24* (2006.01)

(52) U.S. Cl.
USPC .................................. 73/864.33; 73/864.34

(58) Field of Classification Search ............... 73/864.33, 73/864.71
See application file for complete search history.

(56) References Cited

U.S. PATENT DOCUMENTS

| | | | |
|---|---|---|---|
| 5,386,788 A | 2/1995 | Linker et al. | |
| 5,854,431 A | 12/1998 | Linker et al. | |
| 5,915,268 A | 6/1999 | Linker et al. | |
| 6,083,360 A | 7/2000 | Ohlhausen et al. | |
| 6,085,601 A | 7/2000 | Linker et al. | |
| 6,326,615 B1 | 12/2001 | Syage et al. | |
| 6,334,365 B1 | 1/2002 | Linker et al. | |
| 6,345,545 B1 | 2/2002 | Linker et al. | |
| 6,477,907 B1 | 11/2002 | Chambers et al. | |
| 6,523,393 B1 | 2/2003 | Linker et al. | |
| 6,572,825 B1 | 6/2003 | Linker et al. | |
| 6,604,406 B1 | 8/2003 | Linker et al. | |
| 6,617,591 B1 | 9/2003 | Simonson et al. | |
| 6,848,325 B2 | 2/2005 | Parmeter et al. | |
| 6,978,657 B1 | 12/2005 | Baumann et al. | |
| 7,178,379 B1 * | 2/2007 | Strohmeyer et al. | 73/28.01 |
| 7,204,125 B2 * | 4/2007 | Fine et al. | 73/23.41 |
| 7,299,711 B1 | 11/2007 | Linker et al. | |
| 7,401,498 B2 | 7/2008 | Syage et al. | |
| 2004/0022670 A1 | 2/2004 | Megerle et al. | |
| 2006/0060006 A1 * | 3/2006 | Ornath et al. | 73/864.33 |
| 2006/0271211 A1 | 11/2006 | Gleason | |
| 2007/0138387 A1 | 6/2007 | Syage et al. | |

OTHER PUBLICATIONS

Karl A. Hanold, "Mass Spectrometry Base Personnel Screening Portal," Proceedings of the 7$^{th}$ International Symposium in the Analysis and Detection of Explosives, Jun. 25-28, 2001, p. 13, Edinburgh, Scotland.

Kevin L. Linker, "Explosives Detection Personnel Portals," Chapter 12: Counterterrorist Detection Techniques of Explosives, (2007), pp. 367-393.

(Continued)

*Primary Examiner* — Hezron E Williams
*Assistant Examiner* — Nashmiya Fayyaz
(74) *Attorney, Agent, or Firm* — Daniel J. Jenkins (57) ABSTRACT

A portal, system and method for screening an object for a target substance is provided. The portal includes an inflatable bladder expandable to form a test space for receiving the object and a plurality of nozzles positioned about the inflatable bladder. The nozzles are in fluid communication with a fluid source for directing air over the object whereby samples are removed from the object for examination. A collector is operatively connected to the inflatable bladder for collecting the samples removed from the object. A detector is operatively connected to the collector for examining the removed samples for the presence of the target substance. At least one preconcentrator may be operatively connected to the collector for concentrating the samples collected thereby.

33 Claims, 7 Drawing Sheets

OTHER PUBLICATIONS

Jehuda Yinon, "Personal Screening Booths (Portals)", Section 2.10: Forensic and Environmental Detection of Explosives, (1999), pp. 75-79, John Wiley and Sons, West Sussex.

J.E. Parmeter et al, "Testing of a Walk-Through Portal for the Trace Detection of Contraband Explosives", Proceedings of the 2nd Explosives Detection Symposium & Aviation Security Conference, (1996), pp. 187-192, Atlantic City, NJ.

* cited by examiner

SCREENING PORTAL, SYSTEM AND METHOD OF USING SAME

STATEMENT OF GOVERNMENT INTEREST

This invention was developed under Contract DE-AC04-94AL85000 between Sandia Corporation and the U.S. Department of Energy. The U.S. Government has certain rights in the invention.

BACKGROUND OF THE INVENTION

1. Field of the Invention

The present invention relates to techniques for screening objects for target substances. More particularly, the present invention relates to techniques for collecting samples from objects to screen for the presence of target substances, such as explosive materials.

2. Background of the Related Art

Explosive devices pose a significant threat to persons and/or property. In an effort to prevent the unauthorized use of explosive devices, steps are often taken to locate explosive materials, such as C4, TNT, dynamite, fuels, chemicals, casted and/or other volatile materials, before they can be used to cause any damage. In many cases, such explosive materials are hidden or stored to prevent detection. Detectors have been developed to identify the presence of explosive materials as described, for example, in US Patent/Application No. 20060271211, U.S. Pat. Nos. 6,978,657, 6,948,325, 6,617, 591, and 6,477,907. In some cases, only trace amounts of explosive materials may be present. Preconcentrators have been developed for collecting trace amounts of materials as described, for example, in U.S. Pat. Nos. 7,299,711, 6,345, 545, RE38797, 6,617,591, 6,604,406, 6,572,825, 6,523,393, 5,854,431, 6,085,601, 5,854,431 and 6,978,657, the entire contents of which is hereby incorporated by reference.

Techniques have also been developed for screening individuals for the presence of certain materials. In some cases, portals have been developed to perform the screening on humans as described, for example, in U.S. Pat. Nos. 6,334, 365, 5,915,268 and Kevin L. Linker, "Large-Volume Sampling and Preconcentration," 3$^{rd}$ Explosives Detection Technology Symposium and Aviation Security Technology Conference, Atlantic City, N.J., Nov. 26-27, 2001, the entire contents of which are hereby incorporated by reference.

Despite the development of techniques for detecting certain materials, there remains a need to provide advanced systems and methods for screening for target substances, such as explosive or other materials. It may be desirable to provide a system and/or portal that may be easily assembled, disassembled and/or transported between locations for performing screening operations. It may be further desirable to have systems and/or portals that optimize the screening operations. Such optimization may involve, for example, optimized sample removal, optimized efficiency and/or optimized comfort for the object. Preferably, such techniques involve one or more of the following, among others: low cost design and operation, quick operation, high quality sampling, non-contact operation, replaceability of components, optimized air flow, lightweight design, quick assembly/disassembly, accurate detection, additional functions, modularity, replaceable components and/or parts, trace detection capabilities, etc.

BRIEF DESCRIPTION OF THE DRAWINGS

So that the features and advantages of the present invention can be understood in detail, a more particular description of the invention may be had by reference to the embodiments thereof that are illustrated in the appended drawings. These drawings are used to illustrate only typical embodiments of this invention, and are not to be considered limiting of its scope, for the invention may admit to other equally effective embodiments. The figures are not necessarily to scale and certain features and certain views of the figures may be shown exaggerated in scale or in schematic in the interest of clarity and conciseness.

FIG. 1A shows a system comprising a portal having an inflatable bladder and an internal frame. FIG. 1B shows a system comprising a portal having an inflatable bladder and an external frame. FIG. 1C shows a system comprising a portal having a self-standing inflatable bladder, with the collector, detector and electronics removed.

FIGS. 2A-2C are exemplary graphical depictions of the system of FIG. 1C shown in greater detail and with the collector, detector and electronics operatively connected thereto.

DETAILED DESCRIPTION OF THE INVENTION

Presently preferred embodiments of the invention are shown in the above-identified Figures and described in detail below.

Figure 1A:
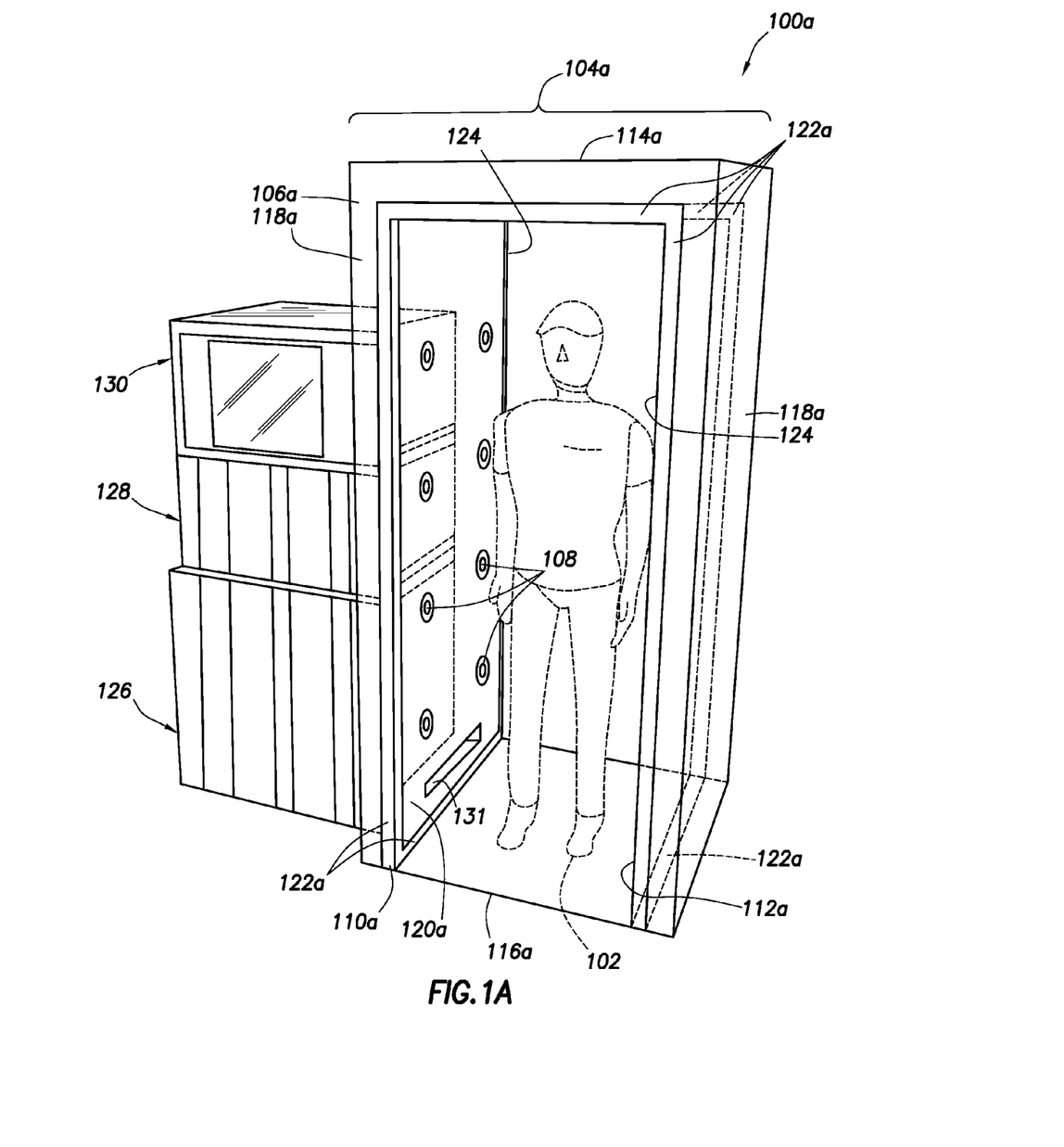
FIGS. 1A-1C are exemplary graphical depictions of a system for screening an object for a target substance, each system comprising a portal, collector, detector and electronics.
Figure 1B:
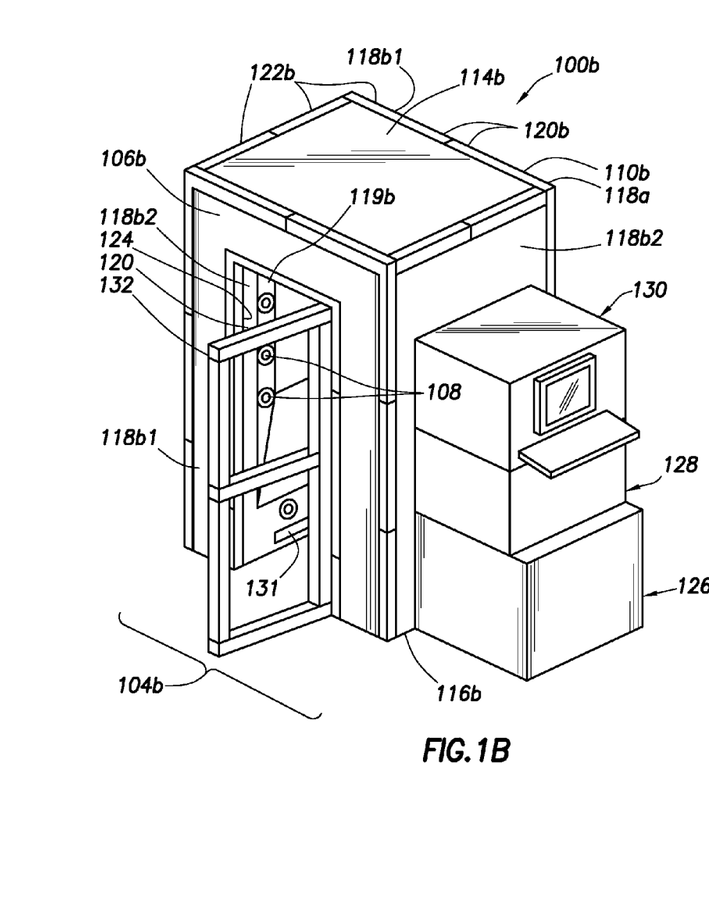
Figure 1C:
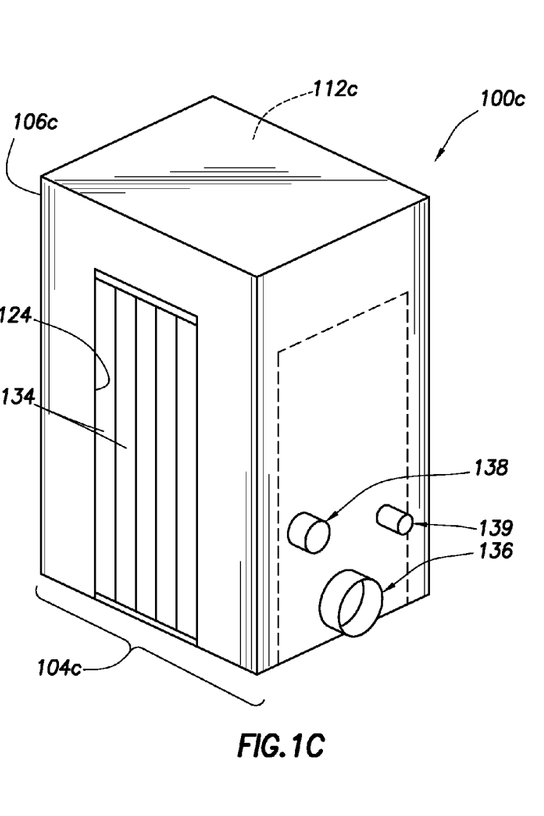

FIGS. 1A-1C show exemplary graphical depictions of a system 100a,b,c, respectively, for screening an object 102 for a target substance. Each system 100a,b,c has a portal 104a,b,c with an inflatable bladder 106a,b,c with a plurality of nozzles 108. In each case, a fluid, such as air, is passed over the object 102 to remove samples for examination. As used herein 'air' shall mean any gas or other fluid that may be passed over the object 102 to release one or more samples therefrom. Such samples may include, for example, particles, vapors or other matter (e.g., lint, hair, dust, etc.) carried by the object. The samples are carried by the air and collected from the portal 104a,b,c for screening as will be described further herein.

As shown in FIG. 1A, the system 100a has a portal 104a with an inflatable bladder 106a and a frame 110a. The inflatable bladder 106a is preferably of a flexible material expandable to define a test space 112a. As shown, the inflatable bladder 106a expands to form a cuboid portal 104a with a top 114a, a bottom 116a and two sides 118a. As seen in this figure, each of the sides 118a of the inflatable bladder 106a are planar and define a flat inner surface 120a having eight nozzles 108. Nozzles 108 may also be placed in the top 114a of the inflatable bladder 106a. Any number of nozzles 108 may be positioned about the portal 104a as desired to facilitate the flow of air over the object 102 such that samples are removed from the object 102.

In the portal 104a of FIG. 1A, the frame 110a is provided to support the inflatable bladder 106a. The frame 110a is preferably made of a material, such as metal, capable of supporting the inflatable bladder 106a in a desired shape. The material is also preferably lightweight, but sturdy for providing support and transportability. As shown in FIG. 1A, the frame 110a includes a plurality of segments 122 fixedly connected, for example, by welding, to form a cuboid-shaped, unitary structure for supporting the inflatable bladder 106a. The frame 110a may be inserted into the inflatable bladder 106a before or after inflation. The inflatable bladder 106a may be connected to the frame 110a using, for example, VELCRO™, straps, ties, adhesive and or other connecting means.

The portal 104a has an opening 124 defining an entrance for receiving the object 102. The object 102 is positioned within a test space 112a in the portal 104a. The portal may be provided with one or more openings 124 for allowing access to the portal 104a. As shown, the portal 104a has two openings 124 to allow a human object 102 to pass therethrough for screening.

The system 100a also includes a collector 126, a detector 128 and electronics 130 operatively connected to the portal 104a. As shown, the collector 126, detector 128 and electronics 130 are positioned in separate containers stacked adjacent the portal 104a. These components are operatively connected to the portal 104a for operation therewith. The collector 126 cycles air through the nozzles 108 and back into the collector 126 via a vent 131 for examination by the detector 128 as will be described further herein.

FIG. 1B shows an alternate system 100b with a portal 104b having an inflatable bladder 106b with an external frame 110b. This system 100b also includes a collector 126, a detector 128 and electronics 130 operatively connected to the portal 104b. In this version, the frame 110b is made of a plurality of segments 122b that are operatively connected to form a collapsible structure. Preferably, the segments 122b releasably lock into place for easy assembly and disassembly. Examples of modular features that may be used are shown in U.S. Pat. No. 5,386,788, the entire contents of which is hereby incorporated by reference. The frame 110b is also provided with a door 132 positioned in the opening 124.

The inflatable bladder 106b has a top 114b, a bottom 116b, two opposing sides 118b1 and two opposing sides 118b2. In this version, side 118b1 is provided with a door 132 positioned in the opening 124 of the inflatable bladder 106b. Rear side 118b1 may also be provided with a door 132, if desired. The other two opposing sides 118b2 define an inner surface 120 with nozzles 108 therein. In this version, the inner surface 119b is convex.

FIG. 1C shows another alternate system 100c including a portal 104c having an inflatable bladder 106c without a frame. The inflatable bladder 106c is expandable into a self-supportable cuboid shaped structure. In this version, the system 110c is shown with the collector 126, a detector 128 and electronics 130 removed from the portal 104c so that collection duct 136, inflation duct 138 and injection duct 139 are visible. The collection duct 136 and injection duct 138 may be used to operatively connect the portal 104c with a collector, such as the collector 126 of FIG. 1A. The inflation duct 139 may be used to operatively connect the portal 104c with a fluid source, such as a blower. The ducts 136, 138, 139 provide fluid communication with portal 104c for the passage of air thereto and therefrom as will be described further herein.

A curtain 134 made of a plurality of strips is positioned in an opening 124 in the portal 106c. The curtain 134 preferably restrict the flow of air from escaping the test space 112c during testing, while permitting access to the test space 112. While curtain 134 is shown in this version, the portal 104c may be provided with curtain 134 and/or a door 132, or neither.

FIGS. 1A-1C depict specific versions of a system 100a,b,c. However, it will be appreciated by one of skill in the art that there may be variations to these systems. For example, while the inflatable bladder and frame are depicted as defining a portal having a cuboid shape, it will be appreciated by one of skill in the art that the portal may be of any shape capable of receiving and screening the object. As shown in these figures, the portals are sized to receive a human as the object, but any size and shape may be used for accommodating any object. One or more doors, curtains or other access means may optionally be placed in one or more openings in the portal. Preferably, at least a portion of the doors and the inflatable bladder are transparent. Also, while various versions of the portal have an internal frame, an external frame or no frame, the inflatable bladder may be provided with zero or more segments and/or frames to support the inflatable bladder in a desired shape. The collector, detector and electronics are shown stacked in separate boxes operatively connectable to the portals, but may be positioned in one or more containers in various configurations separate from or integral with one or more portals 104a,b,c for operation thereof. Other devices, such as ancillary equipment, may be operatively connected to and/or used in connection with the systems 100a,b,c. Various combinations of the systems of FIGS. 1A-1C may be combined to provide the desired configuration.

Figure 2A:
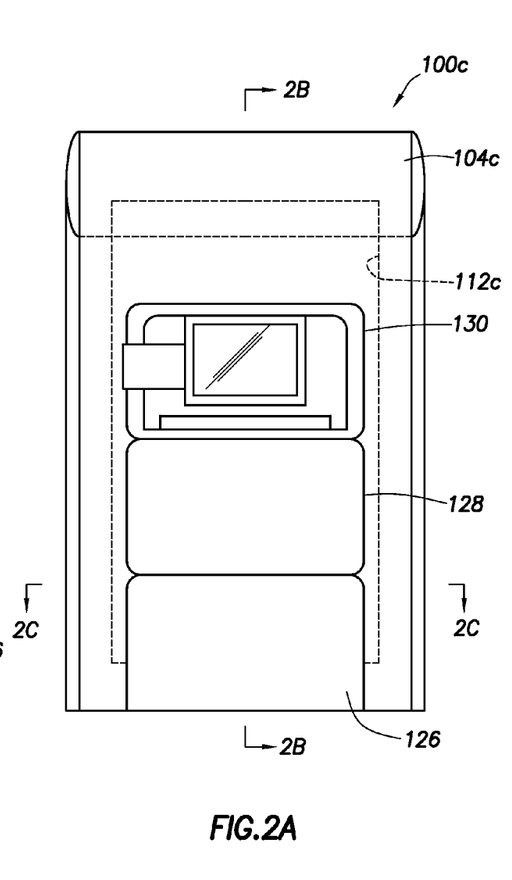
FIG. 2A is a side view of the system of FIG. 1C.
Figure 2B:
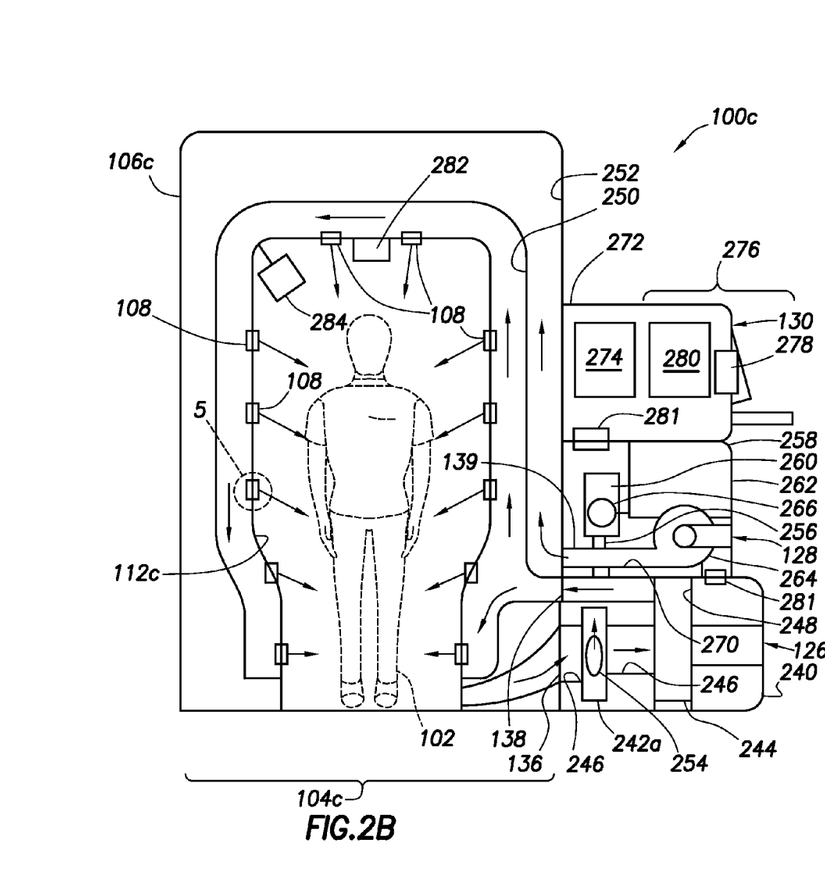
FIG. 2B is a longitudinal cross-sectional view of the system of FIG. 2A taken along line 2B-2B.
Figure 2C:
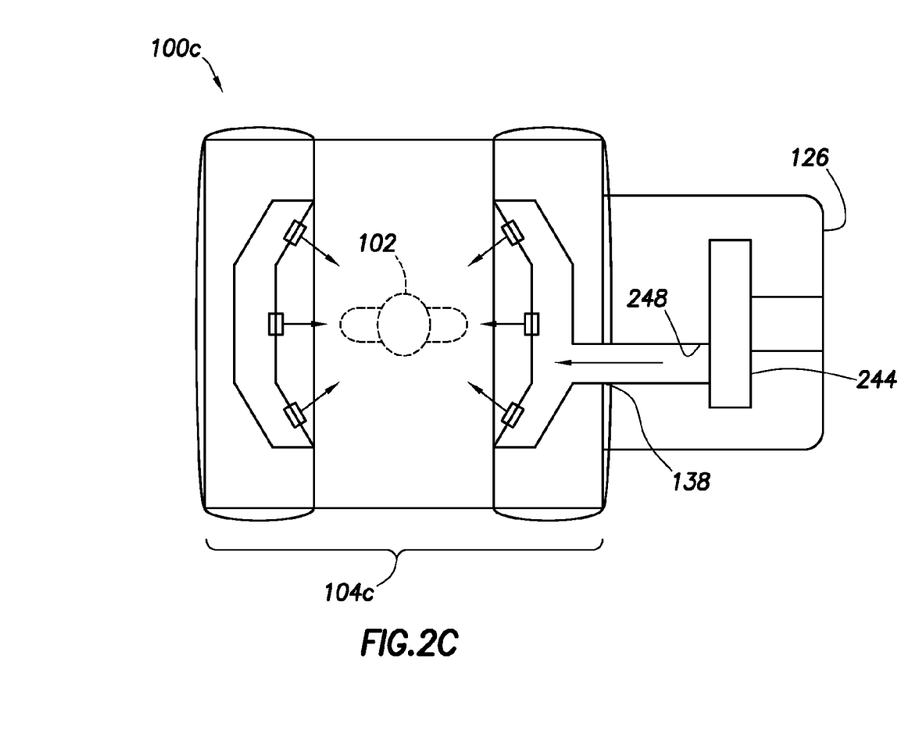
FIG. 2C is a horizontal cross-sectional view of the system of FIG. 2A taken along line 2C-2C.

FIGS. 2A-C show the system 100c of FIG. 1C with the collector 126, detector 128 and electronics 130 connected thereto. FIG. 2A is a side view of the system 100c of FIG. 1C. FIG. 2B is a longitudinal cross-sectional view of the system 100c of FIG. 2A taken along line 2B-2B. FIG. 2C is a horizontal cross-sectional view of the system 100c of FIG. 2A taken along line 2C-2C. These figures depict the operation of the system 100c and the flow of air therethrough for non-contact collection of samples from an object.

As shown in FIG. 2B, the collector 126 is operatively connected to portal 104c via collection duct 136 and injection duct 138 for fluid communication therebetween. The collector 126 includes a collector housing 240 with a first stage preconcentrator 242a and a collection blower 244 therein. The housing 240 has a collector passage 246 in fluid communication with the portal 104a via collection duct 136 for receiving samples therefrom. The passage 246 extends from the portal 104c to the first stage preconcentrator 242a and to the collection blower 244 for the flow of air as shown by the directional arrows. Samples are drawn into collection duct 136 via vent 131 from the portal 104c.

Injection duct 138 passes the recycled air from the collection blower 244 back into the portal via nozzles 108. The recycled air may optionally also be passed into the inflation bladder 104c via injection duct 138 for inflation thereof. Preferably the recycled air is sufficiently cleansed prior to being passed back into the inflation bladder 104c. The preconcentrator 242a may be used to remove contaminants, such as the samples removed from the object, from the recycled air. Other devices, such filters may be used alone or in combination with the preconcentrator to remove such contaminants.

Figure 3A:
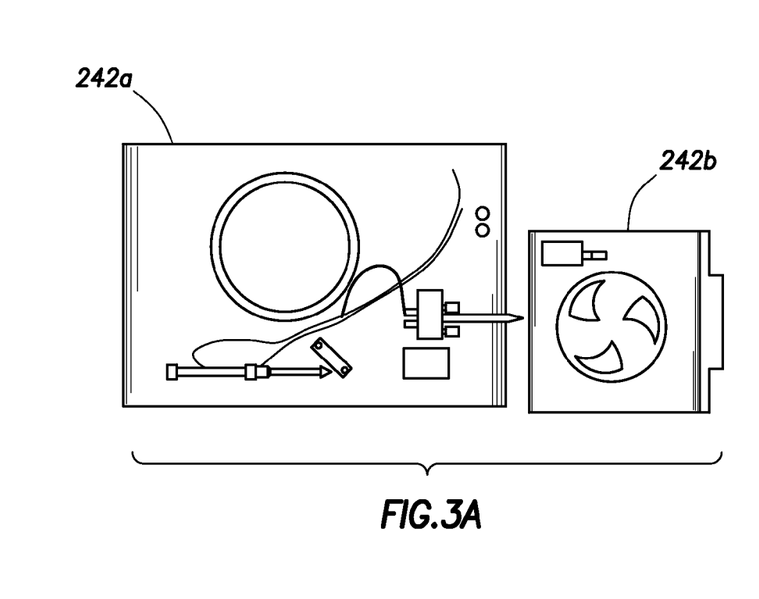
FIGS. 3A and 3B are exemplary schematic depictions of first stage and second stage preconcentrators, respectively, usable with the systems of FIGS. 1A-1C.

The sample(s) received from the portal 104c passes to the first stage preconcentrator 242a via the passage 246. Examples of a first stage preconcentrators are described in U.S. Pat. Nos. 5,854,431 and RE38797, and depicted in FIG.

3A (preconcentrators 242a,b). The first stage preconcentrator 242a captures a portion of the sample passing therethrough to form a test sample 254. The remainder of the air passing through the first stage preconcentrator 242a continues through collector passage 246 to collection blower 244. The collection blower 244 may be used as a fluid pump for drawing fluid from the portal 104c. The collection blower 244 may also be used to generate air flow into the portal 104c. Air generated by the collection blower 244 is passed through a blower passage 248 and back to the portal 104c.

The collection blower 244 is fluidly connected to the inflatable bladder 106c via blower passage 248 extending to duct 136. The inflatable bladder 106c has an inner chamber 250 and an outer chamber 252. The blower passage 248 is fluidly connected with the inner chamber 250 of the inflatable bladder 106c for providing air flow thereto as indicated by the directional arrows. Air is released from the inner chamber 250 and into the test space 112c via nozzles 108.

The configuration of FIGS. 2A-C provides a collection blower 244 that is capable of generating air flow into, and recycling air received from, the inner bladder 106a. It will be appreciated by one of skill in the art that one or more fluid sources, such as a pump, blower or other means, may be used for providing air into the portal and/or receiving air therefrom.

As the air carrying samples pass through the first stage preconcentrator 242a, a portion of the air and samples are collected to form the test sample 254. Once formed in the first stage preconcentrator 242a, the test sample 254 may be passed to the detector 128 via preconcentrator passage 256 extending from the preconcentrator 242a to the detector 128.

The detector 128 includes a housing 258 containing a second stage preconcentrator 260, a sensor 262 and a bladder blower 264. The detector 128 is fluidly connected to the portal via inflation duct 139. Preconcentrator passage 256 establishes fluid communication between the first stage preconcentrator 242a and a second stage preconcentrator 260 for passage of the test sample 254 from the first stage preconcentrator 242a to second stage preconcentrator 260. The second stage preconcentrator 260 further concentrates the test sample 254 by collecting select samples from the test sample 254 to form a concentrated test sample 266. An example of a second stage preconcentrator is described in U.S. Pat. No. 6,345,545, and depicted in FIG. 3B.

Figure 3B:
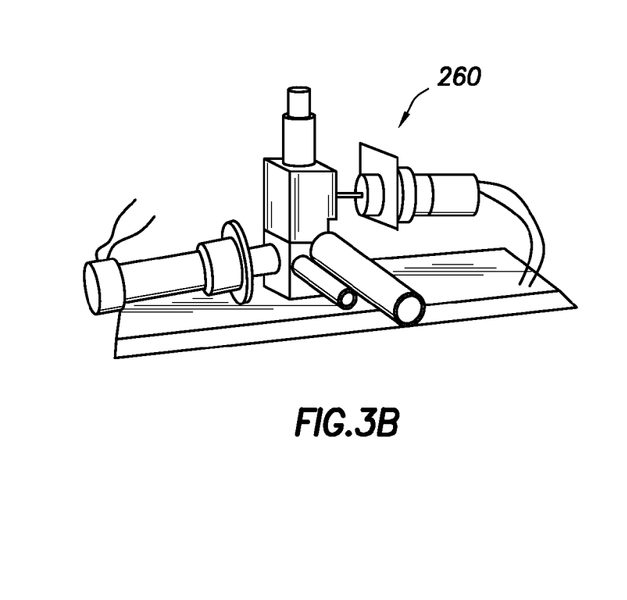

The preconcentrators used herein are preferably configured to collect and/or absorb samples on a mesh and thermally desorb them to the detector. By way of example, the preconcentrator may flow at about 300-500 liters per second. Such flow may be adjusted within this range or to other levels as needed to adequately screen the object. As shown in FIGS. 3A and 3B, a two stage preconcentrator may be used. The first stage of FIG. 3A may have about a 23 cm inlet, and the second state about a 1.2 cm inlet. The two-stage preconcentrator may be used as an impedance matching between large volume sampling requirements and the detector. In some cases, a one stage preconcentrator having about a 15 cm inlet may be used. The thermal desorption used is preferably direct heating utilizing alternating current (AC), but a deep cycle battery for direct current (DC) direct heating may also be used. The operation of preconcentrators are described, for example, in U.S. Pat. Nos. 7,299,711, 6,345,545, RE38797, 6,604,406, 5,854,431, 6,617,591, 6,572,825, 6,523,393, 5,854,431, 6,085,601 and 6,978,657, previously incorporated herein.

Sensor 262 is operatively connected to second stage preconcentrator 260 for sensing parameters of the concentrated test sample 266. The sensor 262 may be any sensor capable of detecting whether the concentrated test sample 266 contains the target substance. The sensor 262 may be one or more sensors, gauges, detectors or other device capable of measuring one or more parameters, such the SMITHS DETECTION™ 400B (commercially available at www.smithdetection.com) capable of detecting explosive material (e.g., TNT, RDX, PETN, HMX, etc.) and ICX NOMADICS™ system (commercially available at www.icxt.com) capable of high vapor detection (e.g., peroxide). One or more sensor 262 may be positioned at various locations for sensing various parameters. The sensor 262 receives and analyzes the concentrated test sample 266 to determine whether the test sample contains the target substance. Some sensors, such as the high vapor detection systems may be used to detect certain materials without a preconcentrator. The sensor 262 may also measure parameters, collect data or otherwise receive information relating to the tests sample, environment, object or other items. Information collected by the sensor 262 may be passed to the electronics 130.

A bladder blower 264 may also optionally be provided in the detector 128. A bladder passage 270 extends from inflation duct 139 to fluidly connect bladder blower 264 to the outer chamber 252 of the inflatable bladder 106c. The bladder blower 264 passes air to the outer chamber 252 to inflate the inflatable bladder 106a and/or maintain its shape. Optionally, the collection blower 244 and/or other means may be used to inflate and/or deflate the inflatable bladder 106c.

Electronics 130 are used to operate the system 100c. Electronics 130 are housed in electronics housing 272. The electronics housing 272 has circuitry 274 and a computer 276 therein for operating the system 100c. The circuitry 274 may be used to provide power and/or communication signals about the system 100c. The computer 276 may be used to collect and analyze data from detector 262, the system 100a, b,c and/or other sources. As shown, the computer 276 is provided with a scanner 278 for collecting information about the object 102. For example, the scanner 278 may provide biometric scans, ID scans, etc. The computer may also be provided with a processor 280 for analyzing the information. The computer 276 may operate independently and/or in combination with other processors and/or computers to perform various functions, such as collecting data, storing data, providing displays, providing reports, etc.

The collector 126, detector 128 and electronics 130 are depicted as being housed in separate housings 240, 258, 272 stacked with connectors 281 therebetween for securing the housings in place. Preferably, these components are stacked with the heaviest container at the bottom. It will be appreciated that the collector, detector and electronics may be positioned in one or more housings about the portal 104a,b,c for operation therewith. The housings 240, 258, 272 may be shipping cases for transporting the contents. Optionally, the housings may be provided with wheels, handles or other items to facilitate operation and/or transport. Preferably, these components and the portal are modular and therefore transportable and/or replaceable.

The portal 104c may be provided with various apparatuses to perform additional functions. For example, the portal 104c is provided with a light 282 for illuminating the portal and a camera 284 for collecting images of the object 102.

As shown in FIGS. 2B and 2C, air flows from the collector 126 through passage 248 and into the inner chamber 250 of the inflatable bladder 106c. The air is directionally released into the test space 112c via nozzles 108. The air is preferably directed from the nozzles 108 downward through the test space 112c such that the air passes over an object 102 to remove samples therefrom.

The air may be selectively directed from the collection blower 244 through the portal 104c. The blower 244 may be used to provide compressed air to the test space 112c. The blower 244 may be used to provide a continuous flow of air through the portal 104c and over the object 102. Preferably, large volume air flow is provided at a high velocity sufficient to remove samples from the object 102. Air is preferably directed downward through the test space 112c as indicated by the arrows. Samples, such as hair, lint and other material are removed by the air flow and gravitational forced, and transported therewith toward the bottom of the portal 104c for removal into the collector 126 via vent 131. The air and samples exit the test space via collection duct 136 and into collector 126. By way of example, samples may be removed at a rate of about 300-500 liters per second, or at other rates as needed.

Figure 4A:
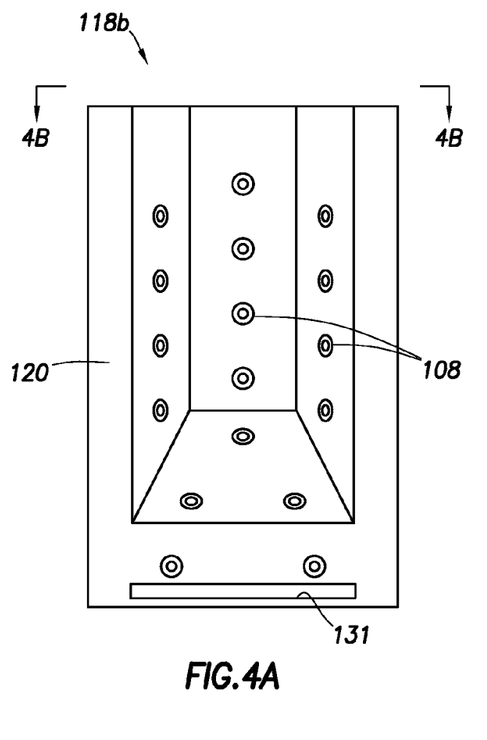
FIG. 4A is a front view of a side of the inflatable bladder of FIG. 1B.
Figure 4B:
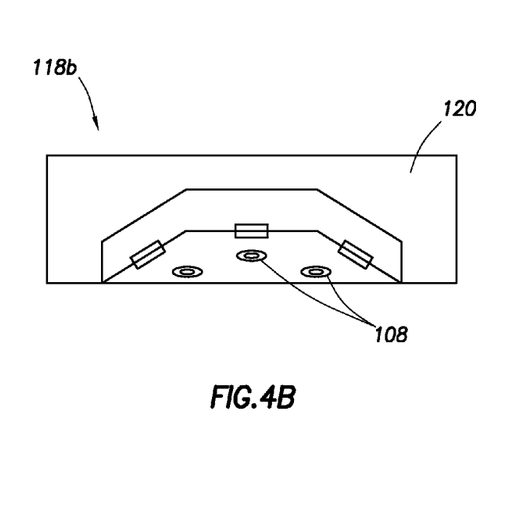
FIG. 4B is a top view of the side of FIG. 4A.

FIG. 4A is a front view of an inner surface 120 of side 118b of the inflatable bladder 104b of FIG. 1B. FIG. 4B is a top view of the inside wall 118b of FIG. 3A. While the sides 112a,b,c may be planar as shown in FIG. 1A, convex as shown in FIG. 1B, or other shape, the sides are preferably shaped to facilitate air flow. As shown in these FIGS. 4A and 4B, the sides 118b of the inflatable bladder 104b are preferably configured to facilitate flow of air about the object 102 during screening. The sides 118b are depicted as having a convex shape with nozzles 108 positioned at various locations thereon. The convex shape is intended to provide a larger test space 112b for the object 102 and to help direct air within the portal 104b. The convex shape of FIGS. 4A and 4B may be used to aim air jets inward toward the object as shown. The side 118b is preferably shaped such that inner surface 120 angles inward and narrow to enhance removal of samples and flow into the vent 131. The nozzles 108 may be placed to further facilitate air flow within the test space 112b (FIG. 1B). The nozzles 108 are preferably directionally adjustable to optimize the air flow and sample removal.

Figure 5:
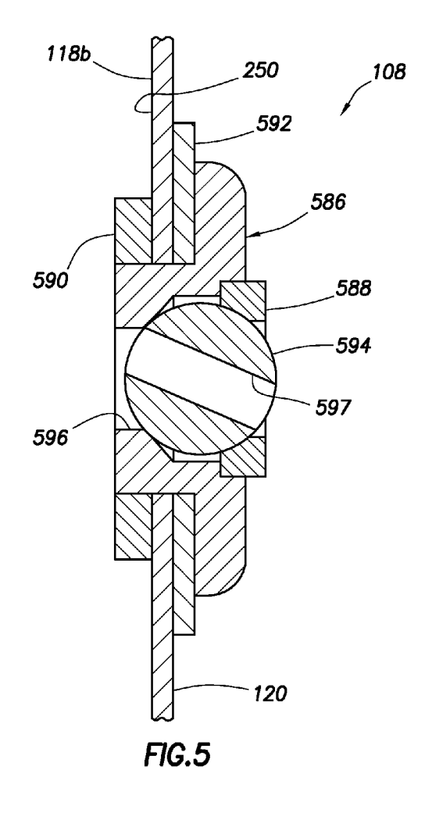
FIG. 5 is a detailed, blown-up view of a section 5 of the inflatable bladder of FIG. 2B.

FIG. 5 is a detailed view of section 5 of FIG. 2B depicting the nozzle 108 in greater detail. The nozzle 108 is preferably a directional nozzle positioned in the side 118b of the inflatable bladder 106b. The nozzle 108 includes a base 586 for supporting the nozzle 108 in the inflatable bladder 106b. Inner and outer locking rings 588, 590 provide further support. Outer locking ring 590 is positioned on an inner surface of side 118b of the inflatable bladder 104b within inner chamber 250. A spacer 592 is positioned between the side 118b and the base 586. An adjustable ball 594 is movably positioned in a base passage 596 in the base 586. The base passage 596 is defined to receive the adjustable ball 594 and allow movement thereof. Inner locking ring 588 is provided to secure the adjustable ball 594 in the base 586. The adjustable ball 594 has a ball passage 597 therethrough for passage of air. In operation, the adjustable ball 594 may be positioned to direct air flow in the desired direction. Preferably, the nozzle 108 is adjustable such that flow of air through the system 100a,b,c is optimized to provide for efficient operation, maximum removal of samples from the object 102, comfort of the object 102, etc. As shown in FIG. 2B, nozzles along the sides may be directed more horizontally toward the object, and nozzles in the top may be directed more vertically downward toward the object. The nozzles as shown and/or other nozzles may be used in connection with systems 100a,b,c.

Figure 6:
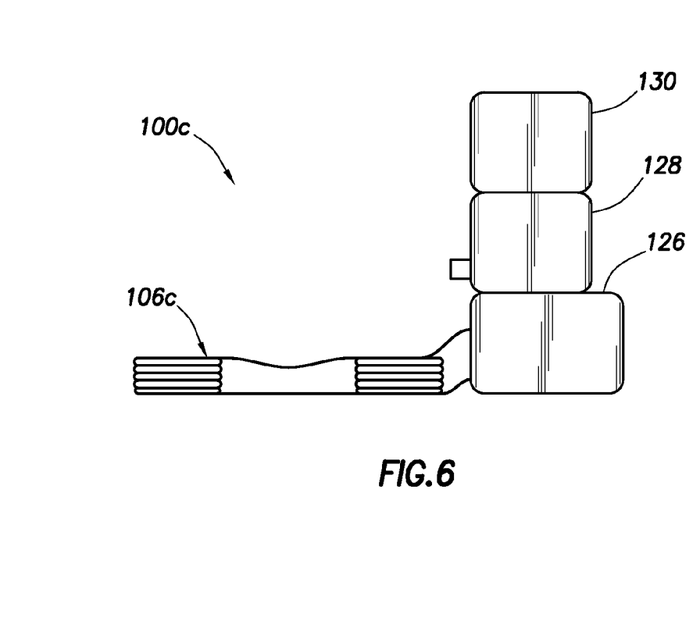
FIG. 6 is a front view of the system of FIG. 2A with the portal in the deflated position.

FIG. 6 is a front view of the system 100c of FIG. 2A. In this figure, the self-standing inflatable bladder 106c is in the deflated position. Preferably, the inflatable bladder 106c deflates to the collapsed position as shown. The inflatable bladder 106c is removable from the collector 126, detector 128 and electronics 130. The inflatable bladder 106c is preferably collapsible for transportation and/or storage.

Figure 7:
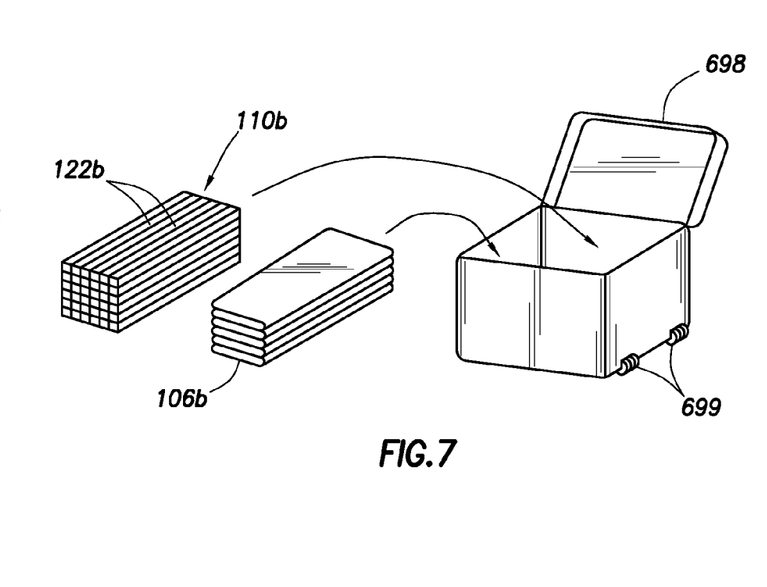
FIG. 7 is an exemplary graphical depiction of a shipping case, and the portal of FIG. 1B in a collapsed position for insertion in the shipping case.

FIG. 7 depicts the system 100b of FIG. 1B in a collapsed position for insertion in a shipping case 698. As shown, the inflatable bladder 106b is collapsed and folded for storage. The segments 122b of frame 110b are also disconnected and stacked for storage. The collapsed inflatable bladder 106b and frame 110b are positionable in the shipping case 698. The shipping case 698 is preferably provided with wheels 699 to facilitate transport. Other features, such as handles, doors, straps, etc., may be provided.

While only the portal 106b is depicted as being collapsed for transport in shipping case 698, it will be appreciated by one of skill in the art that the shipping case 698 may be configured of a desired shape for storing and/or transporting any inflatable bladder, frame and/or other devices. Preferably, the inflatable bladder 106b and/or frame 110b are sufficiently collapsible to fit in the shipping container 698. However, some embodiments may involve non-collapsible items, such as the frame 110a of FIG. 1A. The shipping case 698 with the inflatable bladder and frame therein preferably weighs about 200 pounds (90 kg) or less. Preferably, the shipping case and contents are sufficiently lightweight that they may be loaded and/or transported by a single person.

It will be understood from the foregoing description that various modifications and changes may be made in the preferred and alternative embodiments of the present invention without departing from its true spirit. For example, the portal may be of other shapes to facilitate flow of air about the object.

This description is intended for purposes of illustration only and should not be construed in a limiting sense. The scope of this invention should be determined only by the language of the claims that follow. The term "comprising" within the claims is intended to mean "including at least" such that the recited listing of elements in a claim are an open group. "A," "an" and other singular terms are intended to include the plural forms thereof unless specifically excluded.

What is claimed is:

1. A portal for screening an object for a target substance, the portal comprising:
    an inflatable bladder expandable to form a test space for receiving the object, the test space having a first opening for receiving the object and a second opening for discharging the object; said first and second openings forming a passage through the portal through which the object can pass through the test space; and
    a plurality of nozzles positioned about the inflatable bladder, the plurality of nozzles in fluid communication with a fluid source for directing air over the object whereby samples are removed from the object for examination while the inflatable bladder is expanded; and
    a collector positioned outside the test space and operatively connected to the portal for collecting the samples removed from the object.

2. The portal of claim 1, further comprising a frame for supporting the inflatable bladder.

3. The portal of claim 2, wherein the inflatable bladder is operatively connectable to the frame by one of VELCRO™, straps, ties, and combinations thereof.

4. The portal of claim 2, wherein at least a portion of the frame is positioned within the inflatable bladder.

5. The portal of claim 2, wherein the frame is collapsible.

6. The portal of claim 1, wherein the inflatable bladder is collapsible.

7. The portal of claim 1, wherein at least a portion of the inflatable bladder, when inflated, defines at least one concave surface therein.

8. The portal of claim 1, wherein at least a portion of the inflatable bladder is transparent.

9. The portal of claim 1, wherein the plurality of nozzles direct air downward through the test space.

10. The portal of claim 1, wherein the inflatable bladder is connectable to at least one blower for inflation thereof.

11. The portal of claim 1, wherein the fluid source comprises at least one blower for pumping air through the plurality of nozzles.

12. The portal of claim 1, further comprising a curtain positionable in an opening of the inflatable bladder.

13. The portal of claim 1, further comprising a door positionable in an opening of the inflatable bladder.

14. The portal of claim 1, further comprising at least one sensor operatively connected to the inflatable bladder for measuring parameters thereabout.

15. A system for screening an object for a target substance, the system comprising:
   a portal, comprising;
   an inflatable bladder expandable to form a test space for receiving the object;
   a first opening for receiving the object and a second opening for discharging the object; said first and second openings forming a passage through the portal through which the object can pass through the test space; and
   a plurality of nozzles positioned about the inflatable bladder, the plurality of nozzles in fluid communication with a fluid source for directing air over the object whereby samples are removed from the object for examination while the inflatable bladder is expanded;
   a collector positioned outside the test space and operatively connected to the portal for collecting the samples removed from the object; and
   a detector operatively connected to the collector for examining the removed samples for the presence of the target substance.

16. The system of claim 15, further comprising at least one blower for inflating the inflatable bladder.

17. The system of claim 15, further comprising at least one preconcentrator operatively connectable to the collector for concentrating the samples collected thereby.

18. The system of claim 15, wherein the collector comprises at least one blower for drawing samples into the collector.

19. The system of claim 18, wherein the at least one blower recycles the air back into the portal.

20. The system of claim 18, wherein the blower inflates the inflatable bladder.

21. The system of claim 18, wherein the collector comprises at least one preconcentrator for concentrating the samples received by the collector.

22. The system of claim 15, wherein the detector comprises at least one preconcentrator for concentrating samples collected by the collector.

23. The system of claim 15, wherein the detector comprises at least one sensor for measuring parameters about the portal.

24. The system of claim 15, further comprising electronics for operating one of the portal, the collector, the detector and combinations thereof.

25. The system of claim 24, wherein the electronics comprise a computer operatively connected to the detector.

26. The system of claim 24, wherein the electronics further comprise a scanner for receiving data concerning the object.

27. The system of claim 15, further comprising a sensor positionable about the portal for measuring parameters.

28. A method for screening an object for a target substance, the method comprising:
   inflating an inflatable bladder to form a test space within a portal having a first opening for receiving the object and a second opening for discharging the object; said first and second openings forming a passage through the portal through which the object can pass through the test space;
   receiving the object in the test space;
   directing air from a fluid source and over the object via a plurality of nozzles such that samples are removed from the object while the inflatable bladder is inflated;
   collecting the samples removed from the object in a collector positioned outside of the test space; and
   examining with a detector the collected samples for the presence of the target substance.

29. The method of claim 28, further comprising supporting the inflatable bladder with a frame.

30. The method of claim 28, further comprising concentrating the collected samples using at least one preconcentrator.

31. The method of claim 28, further comprising collecting data relating to the object.

32. The method of claim 28, further comprising collapsing the inflatable bladder for transport.

33. The method of claim 32, further comprising placing the collapsed inflatable bladder in a shipping container.

* * * * *